United States Patent [19]
Wang et al.

[11] Patent Number: 5,942,633
[45] Date of Patent: *Aug. 24, 1999

[54] PROCESS FOR THE SELECTIVE ALKYLATION OF BETAXOLOL INTERMEDIATES

[75] Inventors: Xiu C. Wang; Luping Liu, both of Gurnee; Ashok V. Bhatia, Libertyville, all of Ill.

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/667,038

[22] Filed: Jun. 19, 1996

[51] Int. Cl.$^6$ ........................... C07D 303/18; C07D 93/06
[52] U.S. Cl. ........................... 549/539; 549/512; 564/349
[58] Field of Search ........................... 549/539; 564/349

[56] References Cited

U.S. PATENT DOCUMENTS

| | | | |
|---|---|---|---|
| 3,541,130 | 11/1970 | Koppe et al. | 260/465 |
| 3,663,607 | 5/1972 | Barrett et al. | 260/501.1 |
| 4,018,778 | 4/1977 | Raabe et al. | 260/296 |
| 4,252,984 | 2/1981 | Manoury et al. | |
| 4,760,182 | 7/1988 | Ippolito et al. | |
| 5,034,535 | 7/1991 | Keding et al. | |
| 5,208,352 | 5/1993 | Chen et al. | 549/502 |

FOREIGN PATENT DOCUMENTS 1265523 2/1990 Canada .

OTHER PUBLICATIONS

Askm et al., Tet. Lett. vol. 29, No. 3, pp. 277–280, 1988.
Tanis et al., J. Org. Chem., vol. 53, pp. 4929–4938, 1988.
Antonio Y., et al., "Synthesis of Heteroaromatic Potential β–Adrenergic Antagonists by the Glycidol Route", *Journ of Medicinal Chem*, 21(1):123–126 (1978).
Bachki, A., et al., "Chiral β–Oxidofunctionalised Organolithium Compounds from Epoxides: EPC–Synthesis of 1,3–Diols", *Tetrahedron: Asymmetry*, 6(8):1907–1910 (1995).
Calabretta, R., et al., "Peptidyl and azapeptidyl methylketones as substrate analog inhibitors of papain and cathepsin B", *Eru J Med Chem*, 30:931–941 (1995).
Chiarino, D., et al., "Synthesis of New Isoxazole Aminoalcohols", *Journal Heterocyclic Chem*, 25:337–342 (1988).
Hatakeyama, S., et al., "Preparation of (2R,3S)–1, 2–Epoxypent–4–en–3–ol, a New Chiral Building Block for the Synthesis of (+)–endo– and (−)–exo–Brevicomin", *J. Chem. Soc.*, 1759–1761 (1985).
Kraus, G.A., et al., "Synthetic Studies toward Verrucarol. 1. Synthesis of the AB Ring System", *J. Org. Chem.*, 45:4820–4825 (1980).
Marshall, J.A., et al., "Base–Catalyzed Isomerization of Alkynyloxiranes. A General Synthesis of Furans", *J. Am. Chem. Soc.*, 114:1450–1456 (1992).
Okamura, H., et al., "A Formal Total Synthesis of Aplysiatoxin", *Tetrahedron Letters*, 32(38):5141–5142 (1991).
Schmidhauser, J.C., "A New Preparation of N–Alkyl–2(1H)–pyridones from 2–Glycidoxypyridines", *Tetrahedron Letters*, 32(49):7155–7158 (1991).
Schreiber, S. L., et al., "Studies Relating to the Synthesis of the Immunosuppressive", *J. Org. Chem.*, 54:9–10 (1989).
Seki, T., et al., "Studies on Agents with Vasodilator and β–Blocking Activities. I", *Chem. Pharm. Bull.*, 43(8):1609–1616 (1994).
Takano, S., et al., "A Concise Enantiocontrolled Route to (+)–Patulolide C†", *Heterocycles*, 39(1):67–72 (1994).
Van Hijfte, L., et al., "A Versatile Entry into the Synthesia of α–(Monofluoromethyl) Serine and (E)–Dehydro–α–(monofluoromethyl) Ornithine", *Tetrahedron Letters*, 34(30):4793–4796 (1993).
Okamoto Seutaro et al., "Prostaglandin Synthesis via Two-–Component Coupling. Highly Efficient Synthesis of Chiral Prostaglandin Intermediates 4–Alkoxy–2–alkyl–2–cyclopenten–1–one and 4–Alkoxy–3–alkenyl–2–methylenecyclopentan–1–one", *J. Org. Chem.*, 53:5590–5592 (1988).

*Primary Examiner*—Jose G. Dees
*Assistant Examiner*—Sabiha N. Qazi
*Attorney, Agent, or Firm*—Michael J. Ward; Dugal S. Sickert

[57] ABSTRACT

The present invention relates to a process for the selective alkylation of intermediates of betaxolol.

9 Claims, No Drawings

PROCESS FOR THE SELECTIVE ALKYLATION OF BETAXOLOL INTERMEDIATES

FIELD OF THE INVENTION

The present invention relates to a novel process for the preparation of 1-{4-[2-(Cyclopropylmethoxy)ethyl]phenoxy}-3-isopropylamino-propane-2-ol hydrochloride by selective alkylation of an intermediate alkoxide with an alkylating agent and a base.

BACKGROUND OF THE INVENTION

The processes typically employed in producing 1-{4-[2-(Cyclopropylmethoxy)ethyl]phenoxy}-3-isopropylamino-propane-2-ol (Betaxolol) involved protecting the phenol functional group so that the alcohol could be alkylated. This involves extra protection and subsequent deprotection steps which make the reaction complicated as well as gives low yields which may further require chromatography to purify product.

U.S. Pat. No. 4,252,984 to Manoury et al., describes benzylation of the phenolic alcohol of 4-hydroxyphenethanoic acid. The ethanoic acid group is then reduced to an alcohol and subsequently alkylated with (bromomethyl)cyclopropane. Reduction with $H_2$ in the presence of a catalyst deprotects the compound back to a phenolic compound. In a final step, addition of isopropylamine produces the end product, Betaxolol. A silica gel column is used to purify the compound.

U.S. Pat. No. 4,760,182 to Ippolito et al., describes a process for producing Betaxolol by converting 4-hydroxyphenethanol to a phenoxide anion with a base and then reacting the phenoxide anion with epichlorohydrin to produce 1-[4-(2-hydroxyethyl)phenoxy]-2,3-epoxypropane. 1-[4-(2-hydroxyethyl)phenoxy]-2,3-epoxypropane is reacted with a primary amine to produce an intermediate of Betaxolol. Protection and deprotection steps are necessary to obtain the final product.

U.S. Pat. No. 5,034,535 to Keding et al., describes reacting 4-[2-methoxyethyl]phenol with (S)-5-hydroxymethyl-3-isopropyloxazolidin-2-one sulfonic acid ester to prepare an intermediate in the preparation of S-metoprolol.

The processes typically employed in producing Betaxolol involve extra protection and deprotection steps which make the reaction complicated. Specifically, the epoxide of 1-[4-(2-hydroxyethyl)phenoxy]-2,3-epoxypropane is not stable toward alkylating reagent since the usual alkylation condition will cause polymerization of the epoxy-alcohol. This is due to the molecule possessing both a nucleophilic and an electrophilic center. The alkoxide of 1-[4-(2-hydroxyethyl)phenoxy]-2,3-epoxypropane can react with the alkylating reagent as well as the epoxide moiety of 1-[4-(2-hydroxyethyl)phenoxy]-2,3-epoxypropane, leading to the formation of multiple products/polymers.

It is therefore advantageous and preferable to have a process wherein the protection and deprotection steps can be eliminated. In addition, it would be a further advantage to have a process which produces highly pure betaxolol.

SUMMARY OF THE INVENTION

The present invention relates to a process for the selective alkylation of an alcohol in an epoxy-alcohol compound comprising the steps of reacting the epoxy-alcohol compound in the presence of an alkylating reagent, a solvent and a strong base. The present invention further relates to an improved process for the production of Betaxolol.

DETAILED DESCRIPTION OF THE INVENTION

The present invention relates to a process for producing selective alkylations of alcohol hydroxy groups in compounds which also contain an epoxide functional group. The alcohol hydroxy group of a compound can react with an alkylating reagent in the presence of a strong base without polymerization of the compound due to the reactivity of the epoxide with the alkylating reagent.

The present invention also relates to a novel process for producing intermediates of Betaxolol. The synthetic process for producing intermediates of Betaxolol with the novel alkylation process of the present invention is shown in Scheme 1. The phenolic alcohol of 4-hydroxyphenethanol (1) is usually more readily alkylated than the alcohol hydroxy moiety in the same compound. Typically, for the alcohol hydroxy moiety to be alkylated, the phenolic alcohol had to be protected, thus adding extra protection and deprotection steps.

Such protection and deprotection steps included benzylation of the phenol prior to alkylation of the ethanol moiety and then subsequent hydrogenolysis back to the phenol. After the hydrogenolysis, the epoxide could then be added to the phenol and synthesis of Betaxolol continued. However, with the process of the present invention, such protection and deprotection steps are eliminated. The process of the present invention thus eliminates extra steps also results in higher yields of product.

The selective alkylation of the present invention utilizes a reactive alkylating reagent and a strong base. The present invention relates to a process for producing selective alkylations of alcohol hydroxy groups in compounds which also contain an epoxide functional group. As an example, in the production of the Betaxolol, Betaxolol may be produced in three steps with only one isolation necessary. In Scheme 1, the competition between the reaction of the ethanol hydroxy moiety of 1-[4-(2-hydroxyethyl)phenoxy]-2,3-epoxypropane (2) with an incoming alkylating reagent and with the epoxide of 1-[4-(2-hydroxyethyl)phenoxy]-2,3-epoxypropane (2) was optimized such that self polymerization with the epoxide was eliminated.

Scheme 1.

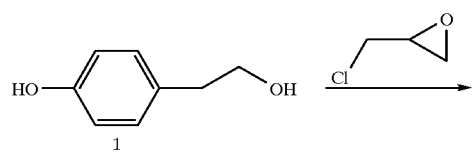

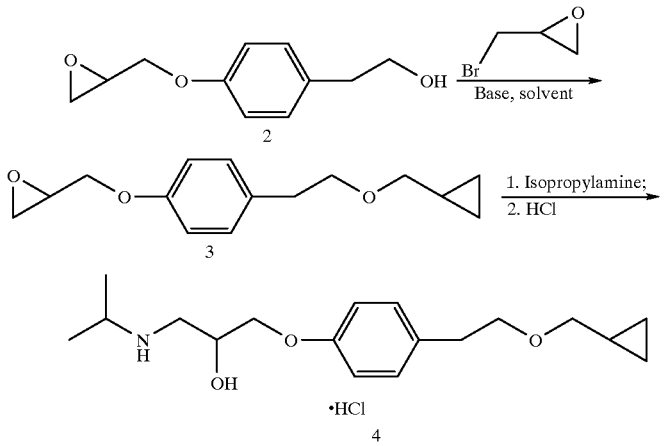

Suitable alkylating agents used in the selective alkylation of the present invention include substituted haloalkyls, halo-substituted cycloalkyls, halo-substituted cycloalkylalkyls, halo-substituted arylalkyls, halo-substituted aryl, halo-substituted alkoxies, halo-substituted arylalkoxies, halo-substituted cycloalkoxies, halo-substituted cycloalkylalkoxies, halo-substituted heterocyclics or halo-substituted (heterocyclic)alkyls. In addition, sulfonated substituted alkylating agents may be used instead of halo-substituted alkylating agents. Alkyl groups include straight or branched chain alkyl radicals containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

Suitable strong bases used in the selective alkylation of the present invention include, but are not intended to be limited to, potassium tert-butoxide, 1,8-Diazabicyclo[5.4.0]undec-ene (DBU), alkyllithiums including, but not limited to butyllithium (BuLi), and lithium diisopropylamide (LDA), and phenyllithium. The most preferred base is potassium tert-butoxide.

Solvents which may be used with the present invention include, but are not intended to be limited to, Dimethyl Sulfoxide (DMSO), N,N-dimethylformamide (DMF), N,N-Dimethylacetamide (DMA), acetonitrile, dichloromethane, ethyl acetate, and tetrahydrofuran (THF).

The temperature of the reaction is typically run at from about −10° C. to about 25° C. A more preferred temperature range is from about −10° C. to about 10° C. A most preferred temperature range is from about −5° C. to about 5° C.

In accordance with the teaching of the present invention, the selective alkylation of 1-[4-(2-hydroxyethyl)phenoxy]-2,3-epoxypropane (2) in the presence of a strong base produces intermediate, 1-{4-[2-(Cyclopropylmethoxy)ethyl]phenoxy}-2,3-epoxypropane (3). 1-{4-[2-(Cyclopropylmethoxy)ethyl]phenoxy}-2,3-epoxypropane may then be reacted with isopropylamine followed by an acid including, but not intended to be limited to, hydrochloric acid to yield Betaxolol (4).

The following example is merely an example of the process of the present invention utilizing the selective alkylation procedure in the presence of a base.

EXAMPLE 1

A reaction flask was charged with 1-[4-(2-Hydroxyethyl)phenoxy]-2,3-epoxypropane (140 grams, 0.72 moles), bromomethylcyclopropane (90 milliliters (mL), 125 grams, 0.92 millimoles) and N,N'-dimethylacetamide (700 mL). The mixture was blanketed with nitogen and stirred at room temperature for 10 minutes and then cooled to 0° C. Potassium tert-butoxide (120 grams, 1.1 moles) was slowly added. After the addition was completed, the reaction mixture was maintained at 0° C. for 3 hours.

The reaction mixture was diluted with aqueous hydrochloric acid (7 Normal, 500 mL). The aqueous mixture was extracted three times with 500 mL portions of heptane. The combined organic extracts were washed twice with 500 mL portions of water and concentrated to an oil by vacuum distallation to give 179 grams (100% yield) of 1-{4-[2-(Cyclopropylmethoxy)-ethyl]-phenoxy}-2,3-epoxypropane which was used for the preparation of Betaxolol without additional purification.

EXAMPLE 2

The oil obtained in Example 1 (179 grams) was dissolved in 400 mL of isopropylamine. After the reaction solution was refluxed for 2 days, the isopropylamine was distilled off and the residue was dissolved in 200 mL of toluene. The toluene was removed by vacuum distillation to give 222 grams of 1-{4-[2-(Cyclopropylmethoxy)ethyl]phenoxy}-3-isopropylamino-propane-2-ol (Betaxolol free base) which was used for the preparation of the hydrochloride salt without additional purification. The Betaxolol free base was dissolved in 300 mL of toluene containg 20 mL of isopropanol. A stream of hydrogen chloride gas was passed through the above solution at 0° C. until the reaction mixture pH was less than 3.0. The solvent was removed by vacuum distillation, and the residue was crystallized from 400 mL of acetone to give 102 grams (99% pure) of Betaxolol hydrochloride.

We claim:

1. A process for the selective alkylation of the ethanol hydroxy moiety 1-[4-(hydroxyethyl)phenoxy]-2,3-epoxypropane comprising the steps of reacting the 1-[4-(hydroxyethyl)phenoxy]-2,3-epoxypropane in the presence of an alkylating reagent, a solvent and a strong base.

2. A process of claim 1 wherein said alkylating agent is selected from the group consisting of: haloalkyls, halo-substituted cycloalkyls, halo-substituted cycloalkylalkyls, halo-substituted arylalkyls, halo-substituted aryl, halo-substituted alkoxies, halo-substituted arylalkoxies, halo-substituted cycloalkoxies, halo-substituted cycloalkylalkoxies, halo-substituted heterocyclics, and halo-substituted (heterocyclic) alkyls.

3. A process of claim 1 wherein said alkylating agent is selected from the group consisting of: sulfonate substituted alkyls, cycloalkyls, cycloalkylalkyls, arylalkyls, aryl, alkoxies, arylalkoxies, cycloalkoxies, cycloalkylalkoxies, heterocyclics, and halo-substituted (heterocyclic)alkyls.

4. A process of claim 1 wherein the temperature of the reaction is carried out at a temperature from below −10° C. to about 25° C.

5. A process of claim 1 wherein the temperature of the reaction is carried out at a temperature from about −10° C. to about 10° C.

6. A process of claim 1 wherein the temperature of the reaction is carried out at a temperature from about −5° C. to about 5° C.

7. A process of claim 1 wherein said strong base is selected from the group consisting of: potassium tert-butoxide, 1,8-Diazabicyclo [5.4.0]undecene, alkyllithium, lithium diisopropylamide, and phenyllithium.

8. A process of claim 1 wherein said solvent is selected from the group consisting of:

Dimethyl Sulfoxide, N,N-dimethylformamide, N,N-Dimethylacetamide, acetonitrile, tetrahydrofuran, 1-methyl-2-piperidone, and 1-methyl-2-pyrrolidone.

9. A process for the production of Betaxolol comprising the steps of:

a). reacting 1-[4-(2-hydroxyethyl)phenoxy]-2,3-epoxypropane with a strong base to produce 1-{4-[2-(Cyclopropylmethoxy)ethyl]phenoxy}-2,3-epoxypropane; and b). reacting 1-{4-[2-(Cyclopropylmethoxy)ethyl]phenoxy}-2,3-epoxypropane with isopropylamine to produce Betaxolol.

* * * * *